(12) United States Patent
Kofod et al.

(10) Patent No.: US 6,242,237 B1
(45) Date of Patent: Jun. 5, 2001

US006242237B1

(54) ENZYME WITH GALACTANASE ACTIVITY

(75) Inventors: Lene Venke Kofod, Uggerløse; Markus Sakari Kauppinen, Copenhagen N; Lene Nonboe Andersen, Allerød; Ib Groth Clausen, Hillerød; Anette Müllertz, Charlottenlund, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/137,855

(22) Filed: Aug. 21, 1998

Related U.S. Application Data

(63) Continuation of application No. PCT/DK97/00092, filed on Feb. 28, 1997.

(30) Foreign Application Priority Data

Mar. 1, 1996 (DK) .................................................. 0233/96
Mar. 1, 1996 (DK) .................................................. 0235/96

(51) Int. Cl.[7] .............................. C12N 9/00; C12N 9/24; C12N 1/20; C12N 15/00; C12P 21/06
(52) U.S. Cl. ...................... 435/200; 435/69.1; 435/183; 435/200; 435/252.3; 435/254.1; 435/320.1
(58) Field of Search ................................... 435/183, 200, 435/201, 202, 203, 207, 209; 536/23.7, 23.74, 23.2

(56) References Cited

FOREIGN PATENT DOCUMENTS

WO 92/13945    8/1992 (DK) .

OTHER PUBLICATIONS

EMBL, Database Genbank/DDBJ, Swissport Accession No. L34599, Jul. 16, 1994.

Chemical Abstracts, 114(21):434 Abstract No. 203206s, 1991.

Yawara et al. (1991). Agnc. Biol. Chem. vol. 55(5):1265–1272.

Tsumuraya Y. et al. (1990). J. Biol. Chem. vol. 265(13):7207–7215.

*Primary Examiner*—Ponnathapu Achutamurthy
*Assistant Examiner*—Manjunath Rao
(74) *Attorney, Agent, or Firm*—Elias J. Lambiris, Esq.; Reza Green, Esq.

(57) ABSTRACT

The present invention relates to an enzyme with galactanase activity, a DNA construct encoding the enzyme with galactanase activity, a method of producing the enzyme, an enzyme composition comprising the enzyme with galactanase activity, and the use of the galactanase enzyme and enzyme composition for a number of industrial applications.

34 Claims, No Drawings

ENZYME WITH GALACTANASE ACTIVITY

This application is a continuation of PCT/DK97/00092 filed Feb. 28, 1997.

FIELD OF INVENTION

The present invention relates to an enzyme with galactanase activity, a DNA construct encoding the enzyme with galactanase activity, a method of producing the enzyme, an enzyme composition comprising said enzyme with galactanase activity, and the use of said enzyme and enzyme composition for a number of industrial applications.

BACKGROUND OF THE INVENTION

Galactans and arabinogalactans are present in most plants as components of pectic hairy regions. They are usually attached to 0–4 of rhamnose residues in the rhamnogalacturonan backbone of the hairy region. The distribution and composition of the sidechains vary considerably between different cell types and physiological states, but in general about half of the rhamnosyl units in the rhamnogalacturonan regions have sidechains attached. The galactan sidechains are in most plants type 1 galactans, which are composed of β-1,4 linked galactopyranose with some branching points and a length of up to 60 saccharide units (DP60). Arabinofuranose residues or short arabinan oligomers can be attached to the galactan chain at the 0–3 of the galactosyl unit, thus named arabinogalactan. Galactans (or arabinogalactans) have an important function in the primary cell wall, where they interact with other structural components of the cell wall such as xyloglucans or arabinoxylans. Thus they possibly serve to anchor the pectic matrix in the cell wall. Furthermore, they increase the hydration and waterbinding capacity and decrease inter-chain association between pectin polymers which is thought to be of importance for modulation of porosity and passive diffusion. (Carpita & Gibeaut, 1993, Plant J.,3, 1–30; O'Neill et al., 1990, Methods in Plant Biochemistry, 415–441; Selvendran, 1983, The Chemistry of Plant Cell Walls. Dietary Fibers; Hwang et al., Food Hydrocolloids, 7, 39–53; Fry, 1988, The growing Plant Cell Wall: Chemical and Metabolic Analysis).

β-1,4-galactanases (E.C.3.2.1.89) degrade galactans (and arabinogalactans) and have been purified from a variety of microbial sources (Nakano et al., 1985, Agric. Biol. Chem., 49, 3445–3454; Emi & Yamamoto, 1972, Agric. Biol. Chem., 36, 1945–1954; Araujo & Ward, 1990, J. Ind. Microbiol., 6, 171–178; Van De Vis et al., 1991, Carbohydr. Polym., 16, 167–187).

The pH optimum of present known fungal galactanases are in the low pH range. Thus, Araujo et al. (J. Industrial Microbiology (1990) 6:171–178) describe a fungal galactanase (*Thielavia terrestris*) with a pH optimum of 5.8; and Hirofumi et al. (Kagaku to Kogyo (science) (science and Industry), (1990) vol. 64, no. 9, pp. 440–445) describe a fungal galactanase from *Aspergillus niger* with a pH optimum around 4.0.

Even though a number of β-1,4-galactanases have been purified, only one has been cloned and DNA sequenced. Thus WO 92/13945 describe cloning and DNA sequencing of a fungal β-1,4-galactanase (*Aspergillus aculeatus*)

The object of the present invention is to provide novel galactanases with a pH optimum in the neutral or alkaline range.

SUMMARY OF THE INVENTION

The present invention is based on the cloning and characterization of two DNA sequence obtained from fungal strains within the order of Sordariales, which both encode fungal enzymes exhibiting galactanase activity and have a pH optimum of at least 5.9.

The galactanases of the invention are the first known and purified fungal galactanases with a pH optimum above 5.8. This is presently believed to be advantageous for a number of industrial applications, such as in the animal feed industry (see e.g. a working example disclosed herein (vide infra)).

Accordingly, in a first aspect the invention relates to a fungal galactanase which has a pH optimum above 5.9.

Further the present inventors have identified two amino acid motifs in the amino acid sequences of the two galactanases obtained from Sordariales. It is presently believed that these motifs are characteristic for galactanases from Sordariales. Degenerated PCR DNA primers have been made based on above mentioned two motifs, and it is presently believed that it is possible to clone other galactanase from Sordariales exhibiting similar characteristic as the two described above. Especially the high pH optimum profile which is advantageous for a number of industrial applications (vide infra).

Accordingly in a further aspect the invention relates to a DNA construct obtained from a fungal strain of the order of Sordariales, encoding an enzyme exhibiting galactanase activity, which DNA sequence hybridizes under low stringency conditions with a probe which is a product of a PCR reaction with DNA isolated from *Humicola insolens* (DSM 1800) and/or with DNA isolated from *Myceliophthora thermophila* (CBS 117.65) and the following pairs of PCR primers:

"5'-CTA TTC GGA TCC AG(C/T) GA(C/T) AC(A/C) TGG GC(G/C) GA(C/T) CC(G/T) GC(G/T) C-3'" [SEQID NO 5] as the sense primer, and "5'-CTA ATG TCT AGA (A/G)AT CCA (A/G/C/T)GC (A/G/C/T)GG (C/T)TC CCA (A/G)TA AAA-3'" [SEQID NO 6] as the anti-sense primer.

In a further aspect the invention relates to a DNA construct comprising a DNA sequence encoding a galactanase enzyme of the invention.

In a further aspect the invention provides a recombinant expression vector, which enables recombinant production of an enzyme of the invention. Thereby it is possible to make a mono-component galactanase composition, which is highly advantageous for a number of industrial applications.

In a further aspect the invention relates to an isolated enzyme exhibiting galactanase activity which comprises the partial amino acid sequence a) Ser(S)-Asp(D)-Thr(T)-Trp(W)-Ala(A)-Asp(D)-Pro(P)-Ala(A)-His(H) and/or Phe(F)-Tyr(Y)-Trp(W)-Glu(E)-Pro(P)-Ala(A)-Trp(W)-Ile(I).

Finally the invention relates to an isolated substantially pure biological culture of the *Saccharomyces cerevisiae* strain DSM No. 9983 harbouring a galactanase encoding DNA sequence (shown in SEQ ID No 1) (the galactanase encoding part of the DNA sequence cloned into plasmid pYES 2.0 present in *Saccharomyces cerevisiae* DSM 9983) derived from a strain of the filamentous fungus *Myceliophthora thermophila,* or any mutant of said *Saccharomyces cerevisiae* strain having retained the galactanase encoding capability; and the invention relates to an isolated substantially pure biological culture of the *Saccharomyces cerevisiae* strain DSM No. 9976 harbouring a galactanase encoding DNA sequence (shown in SEQ ID No 3) (the galactanase encoding part of the DNA sequence cloned into plasmid pYES 2.0 present in *Saccharomyces cerevisiae* DSM 9976) derived from a strain of the filamentous fungus *Humicola insolens* or any mutant of said *Saccharomyces cerevisiae* strain having retained the galactanase encoding capability.

DEFINITIONS

Prior to discussing this invention in further detail, the following terms will first be defined.

"A DNA construct": The term "A DNA construct", refers to a DNA sequence cloned in accordance with standard cloning procedures used in genetic engineering to relocate a segment of DNA from its natural location to a different site where it will be reproduced. The cloning process involves excision and isolation of the desired DNA segment, insertion of the piece of DNA into the vector molecule and incorporation of the recombinant vector into a cell where multiple copies or clones of the DNA segment will be replicated.

The "DNA construct" of the invention may alternatively be termed "cloned DNA sequence" or "isolated DNA sequence".

"Obtained from": For the purpose of the present invention the term "obtained from" as used herein in connection with a specific microbial source, means that the enzyme is produced by the specific source, or by a cell in which a gene from the source have been inserted.

"An isolated polypeptide": As defined herein the term, "an isolated polypeptide" or "isolated galactanase", as used about the galactanase of the invention, is a galactanase or galactanase part preparartion which is at least about 20% pure, preferably at least about 40% pure, more preferably about 60% pure, even more preferably about 80% pure, most preferably about 90% pure, and even most preferably about 95% pure, as determined by SDS-PAGE.
The term "isolated polypeptide" may alternatively be termed "purified polypeptide".

"Homologous impurities": As used herein the term "homologous impurities" means any impurity (e.g. another polypeptide than the enzyme of the invention) which originate from the homologous cell where the enzyme of the invention is originally obtained from. In the present invention the homologous cell may e.g. be a strain of *H. insolens* and/or a strain of *M. thermophilum*.

"Galactanase encoding part": As used herein the term "galactanase encoding part" used in connection with a DNA sequence means the region of the DNA sequence which corresponds to the region which is translated into a polypeptide sequence. In the DNA sequence shown in SEQ ID NO 1 it is the region between the first "ATG" start codon ("AUG" codon in mRNA) and the following stop codon ("TAA", "TAG" or "TGA"). In others words this is the translated polypeptide.

The translated polypeptide comprises, in addition to the mature sequence exhibiting galactanase activity, an N-terminal signal sequence. The signal sequence generally guides the secretion of the polypeptide. For further information see (Stryer, L., "Biochemistry" W. H., Freeman and Company/New York, ISBN 0-7167-1920-7).

In the present context the term "galactanase encoding part" is intended to cover the translated polypeptide and the mature part thereof.

"Galactanase" In the present context galactanase is defined according to the Enzyme classification (EC), as having the EC-number: 3.2.1.89.
Official Name:ARABINOGALACTAN ENDO-1,4-BETA-GALACTOSIDASE.
Alternative Name(s):
ENDO-1,4-BETA-GALACTANASE.
GALACTANASE.
ARABINOGALACTANASE.
Reaction catalysed:
ENDOHYDROLYSIS OF 1,4-BETA-D-GALACTOSIDIC LINKAGES IN ARABINOGALACTANS.

DETAIIED DESCRIPTION OF THE INVENTION

All patents, patent applications, and references disclosed herein are hereby incorporated by reference in their entirety. In the case of conflict, the present disclosure, including definitions, will control.

Fungal Galactanase with a pH Optimum Above 5.9

The present invention provides for the first time a fungal galactanase which has a pH optimum above 5.8.

The expression "pH optimum at 5.9" means that an enzyme of the invention has maximum activity at pH 5.9 compared to the activity at other pH values in the pH interval from 2.5–10.0. The activity is measured as the release of blue colour from AZCL-galactan after 15 minutes of incubation at 30° C. in citrate/phosphate buffers, see Example 3 for further detailed description. Thus, in the present context, the expression "pH optimum above 5.9", means that an enzyme of the invention has maximum activity at a pH value above pH 5.9.

The pH optimum is preferably above 5.9, more preferably above 6.0, more preferably above 6.25, more preferably above 6.5, more preferably above 7.0, more preferably above 7.5. Expressed differently the pH optimum of the galactanase of the invention is preferably in the range of 5.8–10, more preferably of 6.0–10, more preferably of 6.5–10, more preferably of 7.0–10, more preferably of 7.5–10.

Without being limited to any theory it is at present contemplated that a fungal galactanase with a pH optimum above 5.9 can be derived from other fungi. Thus the enzyme can be derived from both a filamentous fungus and a yeast. Preferably the enzyme is derived from a fungus of the order of Sordariales, in particular from a fungus of the genus Humicola, Myceliophthora, Scytalidium, Chaetomium, Melanospora, Cercophora, Gelasinospora, Neurospora, Podospora, or Thielavia. More preferably the galactanase of the invention is cloned from a strain of *Myceliophthora thermophila* or *Humicola insolens*.

DNA Constructs

DNA Construct Encoding A Fungal Galactanase With A pH Optimum Above 5.9

The present invention further provides a DNA construct comprising a DNA sequence encoding an enzyme of the invention exhibiting galactanase activity and having a pH optimum above 5.9.

The DNA sequence may be isolated from an organism producing said enzyme, e.g. by purifying the enzyme, amino acid sequencing, and preparing a suitable probe or PCR primer based on this amino acid sequence.

Other suitable methods for isolating the DNA sequence are described below.

In a specific embodiment the DNA construct of the invention encoding a fungal galactanase with a pH optimum above 5.9 is the DNA constructs defined by features a)–f) which are described in further detail below or the DNA construct according to the third aspect of the invention.

DNA Construct Encoding A Galactanase Defined By Use Of Amino Acids Sequence Motifs Preferably, the DNA construct according to the third aspect of the invention, i.e. the DNA sequence based on hybridization to the PCR probe generated as described above by use of the PCR primers shown in SEQ ID Nos. 5 and 6, encodes an enzyme with galactanase activity, which enzyme comprises the following partial amino acid sequence a) Ser(S)-Asp(D)-Thr(T)-Trp(W)-Ala(A)-Asp(D)-Pro(P)-Ala(A)-His(H) and/or b) Phe(F)-Tyr(Y)-Trp(W)-Glu(E)-Pro(P)-Ala(A)-Trp(W)-Ile(I).

More preferably, the DNA construct encodes an enzyme with galactanase activity which comprises the amino acid sequence SEQ ID NO 2 or SEQ ID No 4.

It is presently believed that the DNA construct according to this aspect may be derived from any of the sources described in further detail below in the section Microbial sources. Preferably, the cloned DNA sequence is derived from a strain of the order Sordariales.

DNA Construct Defined By Reference To SEQ ID NO 1 And 3

In a further aspect, the present invention relates to a DNA construct comprising a DNA sequence encoding an enzyme exhibiting galactanase activity, which DNA sequence comprises (a) the galactanase encoding part of the DNA sequence cloned into plasmid pYES 2.0 present in *Saccharomyces cerevisiae* DSM 9983;

(b) the DNA sequence shown in positions 1–1050 in SEQ ID NO 1 or more preferably 55–1050 or its complementary strand;

(c) an analogue of the DNA sequence defined in (a) or (b) which is at least 70% homologous with said DNA sequence;

(d) a DNA sequence which hybridizes with the DNA sequence shown in positions 1–1050 in SEQ ID NO 1 at low stringency;

(e) a DNA sequence which, because of the degeneracy of the genetic code, does not hybridize with the sequences of (b) or (d), but which codes for a polypeptide having the same amino acid sequence as the polypeptide encoded by any of these DNA sequences; or (f) a DNA sequence which is a allelic form or fragment of the DNA sequences specified in (a), (b), (c), (d), or (e).

Also the present invention relates to a DNA construct comprising a DNA sequence encoding an enzyme exhibiting galactanase activity, which DNA sequence comprises (a) the galactanase encoding part of the DNA sequence cloned into plasmid pYES 2.0 present in *Saccharomyces cerevisiae* DSM 9976;

(b) the DNA sequence shown in positions 1–1047 in SEQ ID NO 3 or more preferably 58–1047 or its complementary strand;

(c) an analogue of the DNA sequence defined in (a) or (b) which is at least 70% homologous with said DNA sequence;

(d) a DNA sequence which hybridizes with the DNA sequence shown in positions 1–1047 in SEQ ID NO 3 at low stringency;

(e) a DNA sequence which, because of the degeneracy of the genetic code, does not hybridize with the sequences of (b) or (d), but which codes for a polypeptide having the same amino acid sequence as the polypeptide encoded by any of these DNA sequences; or (f) a DNA sequence which is a allelic form or fragment of the DNA sequences specified in (a), (b), (c), (d), or (e).

It is presently believed that the galactanase encoding part of the DNA sequence cloned into plasmid pYES 2.0 present in DSM 9983. is identical to the galactanase encoding part of the DNA sequence presented in SEQ ID NO 1.

Accordingly, the terms "the galactanase encoding part of the DNA sequence cloned into plasmid pYES 2.0 present in DSM 9983" and "the galactanase encoding part of the DNA sequence presented in SEQ ID NO 1" may be used interchangeably.

It is presently believed that the galactanase encoding part of the DNA sequence cloned into plasmid pYES 2.0 present in DSM 9976 is identical to the galactanase encoding part of the DNA sequence presented in SEQ ID NO 3.

Accordingly, the terms "the galactanase encoding part of the DNA sequence cloned into plasmid pYES 2.0 present in DSM 9976" and "the galactanase encoding part of the DNA sequence presented in SEQ ID NO 3" may be used interchangeably.

The DNA sequence may be of genomic, cDNA, or synthetic origin or any combination thereof.

The present invention also encompasses a cloned DNA sequence which encodes an enzyme exhibiting galactanase activity having the amino acid sequence set forth as the mature part of SEQ ID NO 2 (i.e. pos. 19–350), which DNA sequence differs from SEQ ID NO 1 by virtue of the degeneracy of the genetic code.

The present invention also encompasses a cloned DNA sequence which encodes an enzyme exhibiting galactanase activity having the amino acid sequence set forth as the mature part of SEQ ID NO 4 (i.e. pos. 19–349), which DNA sequence differs from SEQ ID NO 3 by virtue of the degeneracy of the genetic code.

The DNA sequence shown in SEQ ID NO 1,3 and/or an analogue DNA sequence of the invention may be obtained from a microorganism such as a bacteria, a yeast or a filamentous fungus. Preferably it is obtained from a filamentous fungus and examples of suitable ones are given in the section "Microbial sources" (vide infra).

Alternatively, the analogous sequence may be constructed on the basis of the DNA sequence presented as the galactanase encoding part of SEQ ID No. 1 or 3 e.g be a sub-sequence thereof, and/or by introduction of nucleotide substitutions which do not give rise to another amino acid sequence of the galactanase encoded by the DNA sequence, but which corresponds to the codon usage of the host organism intended for production of the enzyme, or by introduction of nucleotide substitutions which may give rise to a different amino acid sequence.

When carrying out nucleotide substitutions, amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain.

Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford et al., (1991), Protein Expression and Purification 2, 95–107.

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (cf. e.g. Cunningham and Wells, (1989), Science 244, 1081–1085). In the latter technique mutations are introduced at every residue in the molecule, and the resultant mutant molecules are tested for biological (i.e. galactanase) activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (cf. e.g. de Vos et al., (1992), Science 255, 306–312; Smith et al., (1992), J. Mol. Biol. 224, 899–904; Wlodaver et al., (1992), FEBS Lett. 309, 59–64).

The DNA sequence homology referred to in (c) above is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, Aug. 1994, Genetics Computer Group, 575 Science Drive, Madison, Wis., U.S.A. 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the coding region of the analogous DNA sequences referred to above exhibits a degree of identity preferably of at least 70%, more preferably at least 80%, more preferably at least 90%, more preferably at least 95%, more preferably at least 97% with the galactanase encoding part of the DNA sequence shown in SEQ ID No. 1.

The hybridization conditions referred to above to define an analogous DNA sequence as defined in (d) above which hybridizes to the galactanase encoding part of the DNA sequences shown in SEQ ID NO 1, i.e. nucleotides 1–1050, and/or the galactanase encoding part of the DNA sequences shown in SEQ ID NO 3, i.e. nucleotides 1–1047, under at least low stringency conditions, but preferably at medium or high stringency conditions are as described in detail below.

Similarly in the third aspect of the invention, the probe which is a product of a PCR reaction, is hybridizing under at least low stringency conditions, but preferably at medium or high stringency, to a DNA sequence encoding a galactanase obtained from Sordariales, under the conditions which are as described in detail below.

Suitable experimental conditions for determining hybridization at low, medium, or high stringency between a nucleotide probe and a homologous DNA or RNA sequence involves presoaking of the filter containing the DNA fragments or RNA to hybridize in 5×SSC (Sodium chloride/ Sodium citrate, Sambrook et al. 1989) for 10 min, and prehybridization of the filter in a solution of 5×SSC, 5×Denhardt's solution (Sambrook et al. 1989), 0.5% SDS and 100 $\mu$g/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), $^{32}$P-dCTP-labeled (specific activity>1×10$^9$ cpm/$\mu$g) probe for 12 hours at ca. 45° C. The filter is then washed twice for 30 minutes in 2×SSC, 0.5% SDS at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

The DNA sequence encoding a galactanase of the invention can be isolated from the strain *Saccharomyces cerevisiae* DSM No. 9983 and/or *Saccharomyces cerevisiae* DSM No. 9976 using standard methods e.g. as described by Sambrook et al., (1989), Molecular Cloning: A Laboratory Manual. Cold Spring Harbor Lab.; Cold Spring Harbor, N.Y.

The DNA sequence encoding an enzyme exhibiting galactanase activity of the invention can also be isolated by any general method involving cloning, in suitable vectors, a cDNA library from any organism expected to produce the galactanase of interest, transforming suitable yeast host cells with said vectors, culturing the host cells under suitable conditions to express any enzyme of interest encoded by a clone in the cDNA library, screening for positive clones by determining any galactanase activity of the enzyme produced by such clones, and isolating the enzyme encoding DNA from such clones.

A general isolation method has been disclosed in WO 93/11249 or WO 94/14953, the contents of which are hereby incorporated by reference. A more detailed description of the screening method is given a working example herein (vide infra).

Alternatively, the DNA encoding a galactanase of the invention may, in accordance with well-known procedures, conveniently be isolated from a suitable source, such as any of the below mentioned organisms, by use of synthetic oligonucleotide probes prepared on the basis of a DNA sequence disclosed herein. For instance, a suitable oligonucleotide probe may be prepared on the basis of the galactanase encoding part of the nucleotide sequences presented as SEQ ID No. 1 and/or SEQ ID No. 3 or any suitable subsequence thereof, or the basis of the amino acid sequence SEQ ID NO 2 and/or SEQ ID NO 4.

Alternatively, the DNA sequence may be cloned by use of PCR primers prepared on the basis of the DNA sequence disclosed herein, in particular on the basis of the degenerated PCR primers disclosed in the third aspect of the invention.

Microbial Sources

It is at present believed that a cloned DNA sequence according to the invention may be obtained from other microorganisms too. For instance, the DNA sequence may be derived by similarly screening a cDNA library of another microorganism, in particular a fungus, such as a strain of an Aspergillus sp., in particular a strain of *A. aculeatus* or *A. niger*, a strain of Trichoderma sp., in particular a strain of *T. reesei*, *T. viride*, *T. longibrachiatum*, *T. harzianum* or *T. koningii* or a strain of a Fusarium sp., in particular a strain of *F. oxysporum*, or a strain of a Humicola sp., or a strain of a Neocallimastix sp., a Piromyces sp., a Penicillium sp., an Aureobasidium sp., a Thermoascus sp., a Paecilomyces sp., a Talaromyces sp., a Magnaporthe sp., a Schizophyllum sp., a Filibasidium sp., or a Cryptococcus sp.

In a preferred embodiment, a cloned DNA sequence encoding a galactanase of the invention is obtained from a strain belonging to the family Sordariales, such as the genera Humicola, Myceliophthora, or Thielavia, in particular a strain of *H. insolens* or *M. thermophilum*.

The expression plasmid pYES 2.0 comprising the full length DNA sequence (shown in SEQ ID NO 1) encoding a galactanase of the invention has been transformed into a strain of the *Saccharomyces cerevisiae* which was deposited by the inventors according to the Budapest Treaty on the International Recognition of the Deposit of Microorganisms for the Purposes of Patent Procedure at the Deutshe Sammlung von Mikroorganismen und Zellkulturen GmbH., Masheroder Weg 1b, D-38124 Raunschweig, Federal Republic of Germany, (DSM).

Deposit date: Nov. 5, 1995

Depositor's ref.: NN049019

DSM designation: *Saccharomyces cerevisiae* DSM No. 9983

The expression plasmid pYES 2.0 comprising the full length cDNA sequence (shown in SEQ ID NO 3) encoding a galactanase of the invention has been transformed into a strain of the *Saccharomyces cerevisiae* which was deposited by the inventors according to the Budapest Treaty on the International Recognition of the Deposit of Microorganisms for the Purposes of Patent Procedure at the Deutshe Sammlung von Mikroorganismen und Zellkulturen GmbH., Masheroder Weg 1b, D-38124 Raunschweig, Federal Republic of Germany, (DSM).

Deposit date: 11.05.95

Depositor's ref.: NN049018

DSM designation: *Saccharonyces cerevisiae* DSM No. 9976

Expression Vectors

In another aspect, the invention provides a recombinant expression vector comprising the DNA construct of the invention.

The expression vector of the invention may be any expression vector that is conveniently subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector, the DNA sequence encoding the galactanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the galactanase, the promoter and the terminator, respectively, and to insert them into suitable vectors are well known to persons skilled in the art (cf., for instance, Sambrook et al., (1989), Molecular Cloning. A Laboratory Manual, Cold Spring Harbor, N.Y.).

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (gluA), *Rhizomucor miehei* lipase, *Aspergillus oryzae* alkaline protease, *Aspergillus oryzae* triose phosphate isomerase or *Aspergillus nidulans* acetamidase.

Host Cells

In yet another aspect the invention provides a host cell comprising the DNA construct of the invention and/or the recombinant expression vector of the invention.

The choice of host cell will to a large extent depend upon the gene encoding the polypeptide and its source. The host cell may be a unicellular microorganism, e.g. a prokaryote, or a non-unicellular microorganism, e.g. a eukaryote.

Preferably, the host cell of the invention is a eukaryotic cell, in particular a fungal cell such as a yeast or filamentous fungal cell. In particular, the cell may belong to a species of Trichoderma, preferably *Trichoderma harzianum* or *Trichoderma reesei*, or a species of Aspergillus, most preferably *Aspergillus oryzae* or *Aspergillus niger*, or a species of Fusarium, most preferably a Fusarium sp. having the identifying characteristic of Fusarium ATCC 20334, as further described in PCT/US/95/07743.

Fungal cells may be transformed by a process involving protoplast formation and transformation of the protoplasts followed by regeneration of the cell wall in a manner known per se. The use of Aspergillus as a host microorganism is described in EP 238 023 (Novo Nordisk A/S), the contents of which are hereby incorporated by reference. The host cell may also be a yeast cell, e.g. a strain of Saccharomyces, in particular *Saccharomyces cerevisae*, *Saccharomyces kluyveri* or *Saccharomyces uvarum*, a strain of Schizosaccharomyces sp., such as *Schizosaccharomyces pombe*, a strain of Hansenula sp., Pichia sp., Yarrowia sp., such as *Yarrowia lipolytica*, or Kluyveromyces sp., such as *Kluyveromyces lactis*.

Method of Producing Galactanase

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified galactanase composition, characterized in being free from homologous impurities.

In the present invention the homologous host cell may e.g. be a strain of *H. insolens* or *M. thermophilum*.

The medium used to culture the transformed host cells may be any conventional medium suitable for growing the host cells in question. The expressed galactanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme of the Invention

In a further aspect the invention relates to an isolated enzyme exhibiting galactanase activity, characterized in (i)

being free from homologous impurities and (ii) said enzyme is produced as described above using a heterologous host cell.

In a still further aspect the invention relates to an isolated enzyme exhibiting galactanase activity which comprises the partial amino acid sequence a) Ser(S)-Asp(D)-Thr(T)-Trp(W)-Ala(A)-Asp(D)-Pro (P)-Ala(A)-His(H) and/or b) Phe(F)-Tyr(Y)-Trp(W)-Glu(E)-Pro(P)-Ala(A)-Trp (W)-Ile(I). Preferably, the enzyme according to this embodiment has the properties a)–d) of the enzymes described immediately below.

In a still further aspect the invention relates to an isolated enzyme exhibiting galactanase activity selected from the group consisting of:

(a) a polypeptide encoded by the galactanase enzyme encoding part of the DNA sequence cloned into plasmid pYES 2.0 present in *Saccharomyces cerevisiae* DSM 9983;

(b) a polypeptide comprising an amino acid sequence as shown in positions 19–350 of SEQ ID NO 2;

(c) an analogue of the polypeptide defined in (a) or (b) which is at least 70% homologous with said polypeptide; and (d) an allelic form or fragment of (a), (b) or (c).

In a still further aspect the invention relates to an isolated enzyme exhibiting galactanase activity selected from the group consisting of:

(a) a polypeptide encoded by the galactanase enzyme encoding part of the DNA sequence cloned into plasmid pYES 2.0 present in *Saccharomyces cerevisiae* DSM 9976;

(b) a polypeptide comprising an amino acid sequence as shown in positions 19–349 of SEQ ID NO 4;

(c) an analogue of the polypeptide defined in (a) or (b) which is at least 70% homologous with said polypeptide; and an allelic form or fragment of (a), (b) or (c).

The polypeptide homology referred to above (property (c)) of the polypeptide(s) of the invention is determined as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., U.S.A. 53711) (Needleman, S. B. and Wunsch, C. D., (1970), Journal of Molecular Biology, 48, 443–453). Using GAP with the following settings for polypeptide sequence comparison: GAP creation penalty of 3.0 and GAP extension penalty of 0.1, the mature part of a polypeptide encoded by an analogous DNA sequence of the invention exhibits a degree of identity preferably of at least 70%, more preferably at least 80%, more preferably at least 90%, more preferably at least 95%, and especially at least 97% with the mature part of the amino acid sequence shown in SEQ ID NO 2, i.e. position 19–350 in SEQ ID NO 2 and/or with the mature part of the amino acid sequence shown in SEQ ID NO 4, i.e. position 19–349 in SEQ ID NO 4.

The present invention is also directed to galactanase variants which have an amino acid sequence which differs by no more than three amino acids, preferably by no more than two amino acids, and more preferably by no more than one amino acid from the mature part of the amino acid sequence set forth in SEQ ID NO 2 and/or SEQ ID NO 4.

The enzyme of the invention may be derived from any of the sources described in the section entitled "Microbial Sources".

Enzyme Compositions

In a still further aspect, the present invention relates to an enzyme composition useful for the degradation of plant cell wall components, said composition being enriched in an enzyme exhibiting galactanase activity as described above. In this manner a boosting of the cell wall degrading ability of the enzyme composition can be obtained.

The enzyme composition having been enriched with an enzyme of the invention may e.g. be an enzyme composition comprising multiple enzymatic activities, in particular an enzyme composition comprising multiple plant cell wall degrading enzymes such as Biofeed+®, Biofeed Wheat®, Energex®, Viscozym®, Pectinex®, Pectinex Ultra SP®, Phytase Novo®, Celluclast or Celluzyme (all available from Novo Nordisk A/S.

In the present context, the term "enriched" is intended to indicate that the galactanase activity of the enzyme composition has been increased, e.g. with an enrichment factor of 1.1, conveniently due to addition of an enzyme of the invention prepared by the method described above. The enzyme composition of the invention may, in addition to a galactanase of the invention, contain one or more other enzymes, for instance those with, xylanolytic, or pectinolytic activities such as α-arabinosidase, α-glucuronisidase, β-xylosidase, xylan acetyl esterase, arabinanase, rhamnogalacturonase, pectin acetylesterase, phytase, galactanase, polygalacturonase, pectin lyase, pectate lyase, glucanase, pectin methylesterase, laccase, or oxidoreductase. The additional enzyme(s) may be producible by means of a microorganism belonging to the genus Aspergillus, preferably *Aspergillus niger*, *Aspergillus aculeatus*, *Aspergillus awamori* or *Aspergillus oryzae*, or Trichoderma, or *Humicola insolens*.

Alternatively, the enzyme composition enriched in an enzyme exhibiting galactanase activity may be one which comprises an enzyme of the invention as the major enzymatic component, e.g. a mono-component enzyme composition.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Examples are given below of preferred uses of the enzyme composition of the invention. The dosage of the enzyme composition of the invention and other conditions under which the composition is used may be determined on the basis of methods known in the art.

The enzyme composition according to the invention may be useful for at least one of the following purposes.

Degradation or Modification of Plant Material

The enzyme composition according to the invention is preferably used as an agent for degradation or modification of plant cell walls or any galactan-containing material originating from plant cells walls due to the high plant cell wall degrading activity of the galactanase of the invention.

The galactanase of the invention hydrolyse b-1,4 linkages in galactanss. Galactans are polysaccharides having a backbone composed of b-1,4 linked galactose. The backbone may have side-branches such as arabinose. The composition and number of side-branches vary according to the source of the galactan. (Stephen, A. M., 1983, ch. 3 in The Polysaccharides, Vol 2, Ed. Aspinall, G. O.).

The degradation of galactan by galactanases is facilitated by full or partial removal of the sidebranches. Arabinose side-groups can be removed by a mild acid treatment or by alpha-arabinosidases. The oligomers with are released by the galactanase or by a combination of galactanases and sidebranch-hydrolysing enzymes as mentioned above can be further degraded to free galactose by beta-galactosidases.

The galactanase of the present invention can be used without other pectinolytic or hemicellulytic enzymes or with limited activity of other pectinolytic or hemicellulytic enzymes to degrade galactans for production of oligosaccharides. The oligosaccharides may be used as bulking agents, like arabinogalactan oligosaccharides released from soy cell wall material, or of more or less purified arabinogalactans from plant material.

The galactanase of the present invention can be used in combination with other pectinolytic or hemicellulytic enzymes to degrade galactans to galactose and other monosaccharides.

The galactanase of the present invention may be used alone or together with other enzymes like glucanases, pectinases and/or hemicellulases to improve the extraction of oil from oil-rich plant material, like soy-bean oil from soybeans, olive-oil from olives or rapeseed-oil from rape-seed or sunflower oil from sunflower.

The galactanase of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions, The separation process may be performed by use of methods known in the art.

The galactanase of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearance of processed fruit or vegetables. The consistency and appearence has been shown to be a product of the actual combination of enzymes used for processing, i.e. the specificity of the enzymes with which the galactanase of the invention is combined. Examples include the production of clear juice e.g. from apples, pears or berries; cloud stable juice e.g. from apples, pears, berries, citrus or tomatoes; and purees e.g. from carrots and tomatoes.

The galactanase of the invention may be used in modifying the viscosity of plant cell wall derived material. For instance, the galactanase may be used to reduce the viscosity of feed which contain galactan and to promote processing of viscous galactan containing material. The viscosity reduction may be obtained by treating the galactan containing plant material with an enyme preparation of the invention under suitable conditions for full or partial degradation of the galactan containing material.

The galactanase can be used e.g. in combination with other enzymes for the removal of pectic substances from plant fibres. This removal is essential e.g. in the production of textile fibres or other cellulosic materials. For this purpose plant fibre material is treated with a suitable amount of the galactanase of the invention under suitable conditions for obtaining full or partial degradation of pectic substances associated with the plant fibre material.

Animal Feed Additive

Galactanases of the present invention may be used for modification of animal feed and may exert their effect either in vitro (by modifying components of the feed) or in vivo. The galactanase is particularly suited for addition to animal feed compositions containing high amounts of arabinogalactans or galactans, e.g. feed containing plant material from soy bean, rape seed, lupin etc. When added to the feed the galactanase significantly improves the in vivo break-down of plant cell wall material, whereby a better utilization of the plant nutrients by the animal is achieved. Thereby, the growth rate and/or feed conversion ratio (i.e. the weight of ingested feed relative to weight gain) of the animal is improved. For example the indigestible galactan is degraded by galactanase, e.g. in combination with β-galactosidase, to galactose or galactooligomers which are digestible by the animal and thus contribute to the available energy of the feed. Also, by the degradation of galactan the galactanase may improve the digestibility and uptake of non-carbohydrate feed constituents such as protein, fat and minerals.

For further description reference is made to PCT/DK 96/00443 and a working example herein (vide infra).

Wine and Juice Processing

An enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

Advantage of Monocomponent Galactanase

From the foregoing it will be apparent that the galactanase of the invention may be produced as a single component enzyme preparation essentially free from other enzyme activies such as pectin methylesterase and other pectinolytic enzymes normally found to be present in commercially available galactanase containing pectinolytic, hemicellulolytic or cellulolytic enzyme preparations.

For this reason the use of the galactanase of the invention is especially advantageous for purposes in which the action of such other enzyme activities are undesirable. Examples include the production of cloud stable juices and the production of purees. In these productions the presence of, e.g. pectin methyl esterase normally found as a sideactivity in conventional pectinolytic enzyme preparations results in a decreased stability of the cloud in cloud stable juice or causes syneresis in puree.

Furthermore, due to its substantial purity the galactanase of the invention can be used to modify pectin in such a way that only the parts of the pectin which contain galactan will be degraded. If conventional pectinolytic activities were present a more extensive degradation of the pectin would be obtained with a resulting reduction in the viscosifying or gelling ability of the pectin.

Finally, the substantially pure galactanase can be used to selectively release galactose and galactooligomers from plant material used for feed. Galactose is readily digested by animals. Conventional pectinolytic or hemicellulolytic enzyme preparations with galactanase activity in addition to the galactanase contain a mixture of endo- and exo-enzymes which produce, e.g. xylose and galacturonic acid which are undesirable in feed.

The invention is described in further detail in the following examples which are not in any way intended to limit the scope of the invention as claimed.

MATERIALS AND METHODS

Deposited Organisms

*Saccharomyces cerevisiae* DSM 9983 containing the plasmid comprising the full length DNA sequence, coding for a galactanase of the invention (shown in SEQ ID NO 1), in the shuttle vector pYES 2.0.

*Saccharomyces cerevisiae* DSM 9976 containing the plasmid comprising the full length cDNA sequence, coding for a galactanase of the invention (shown in SEQ ID NO 3), in the shuttle vector pYES 2.0.

Other Strains

*Myceliophthora thermophila* CBS No. 117.65 comprises the galactanase encoding DNA sequence of the invention (shown in SEQ ID NO 1).

*Humicola insolens* DSM No. 1800 comprises a galactanase encoding DNA sequence of the invention (shown in SEQ ID NO 3).

Yeast strain: The *Saccharomyces cerevisiae* strain used was W3124 (MATa; ura 3-52; leu 2-3, 112; his 3-D200; pep 4-1137; prc1::HIS3; prb1:: LEU2; cir+).

*E. Coli* strain: DH5a (Life Technologies A/S)

Plasmids:

The Aspergillus expression vector pHD414 is a derivative of the plasmid p775 (described in EP 238 023). The construction of pHD414 is further described in WO 93/11249.

pYES 2.0 (Invitrogen)

General molecular biology methods:

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA manipulations

Unless otherwise mentioned all enzymes for DNA manipulations, such as e.g. restriction endonucleases, ligases etc., are obtained from New England Biolabs, Inc.

Fermentation procedure of *Humicola Insolens* DSM 1800 for mRNA isolation:

*Humicola insolens* DSM 1800 was inoculated from a plate with outgrown mycelium into a shake flask containing 100 ml maize- grits containing medium PD liquid broth (24 g potato dextrose broth, Difco 0549, deionized water up to 1000 ml; autoclave (121° C. for 15–20 min)).

The culture was fermented at 26° C. for 5 days. The resulting culture broth was filtered through miracloth and the mycelium was frozen down in liquid nitrogen.

mRNA was isolated from mycelium from this culture as described in (H. Dalboege et al Mol. Gen. Genet (1994) 243:253–260.; WO 93/11249; WO 94/14953).

Fermentation procedure of *Myceliophtora thermophila* CBS No 117.65 for mRNA isolation:

*Myceliophtora thermophila* CBS No. 117.65 was inoculated from a plate with outgrown mycelium into a shake flask containing 100 ml cellulose-containing medium PD liquid broth (24 g potato dextrose broth, Difco 0549, deionized water up to 1000 ml; autoclave (121° C. for 15–20 min)).

The culture was fermented at 26° C. for 5 days. The resulting culture broth was filtered through miracloth and the mycelium was frozen down in liquid nitrogen.

mRNA was isolated from mycelium from this culture as described in (H. Dalboege et al Mol. Gen. Genet (1994) 243:253–260.; WO 93/11249; WO 94/14953).

Extraction of total RN is performed with guanidinium thiocyanate followed by ultracentrifugation through a 5.7 M CsCl cushion, and isolation of poly(A)$^+$RNA is carried out by oligo(dT)-cellulose affinity chromatography using the procedures described in WO 94/14953.

cDNA synthesis: Double-stranded cDNA is synthesized from 5 mg poly(A)$^+$ RNA by the RNase H method (Gubler and Hoffman (1983) Gene 25:263–269, Sambrook et al. (1989) Molecular cloning: A laboratory manual, Cold Spring Harbor lab., Cold Spring Harbor, N.Y.). The poly(A)$^+$ RNA (5 mg in 5 ml of DEPC-treated water) is heated at 70° C. for 8 min. in a pre-siliconized, RNase-free Eppendorph tube, quenched on ice and combined in a final volume of 50 ml with reverse transcriptase buffer (50 mM Tris-Cl, pH 8.3, 75 mM KCl, 3 mM MgCl$_2$, 10 mM DTT, Bethesda Research Laboratories) containing 1 mM of dATP, dGTP and dTTP and 0.5 mM 5-methyl-dCTP (Pharmacia), 40 units human placental ribonuclease inhibitor (RNasin, Promega), 1.45 mg of oligo(dT)$_{18}$-Not I primer (Pharmacia) and 1000 units SuperScript II RNase H reverse transcriptase (Bethesda Research Laboratories). First-strand cDNA is synthesized by incubating the reaction mixture at 45° C. for 1 hour. After synthesis, the mRNA:cDNA hybrid mixture is gelfiltrated through a MicroSpin S-400 HR (Pharmacia) spin column according to the manufacturer's instructions.

After the gelfiltration, the hybrids are diluted in 250 ml second strand buffer (20 mM Tris-Cl, pH 7.4, 90 mM KCl, 4.6 mM MgCl$_2$, 10 mM (NH$_4$)$_2$SO$_4$, 0.16 mM bNAD+) containing 200 mM of each dNTP, 60 units *E. coli* DNA polymerase I (Pharmacia), 5.25 units RNase H (Promega) and 15 units *E. coli* DNA ligase (Boehringer Mannheim). Second strand cDNA synthesis is performed by incubating the reaction tube at 16° C. for 2 hours and additional 15 min. at 25° C. The reaction is stopped by addition of EDTA to a final concentration of 20 mM followed by phenol and chloroform extractions. Mung bean nuclease treatment: The double-stranded cDNA is precipitated at −20° C. for 12 hours by addition of 2 vols 96% EtOH, 0.2 vol 10 M NH$_4$Ac, recovered by centrifugation, washed in 70% EtOH, dried and resuspended in 30 ml Mung bean nuclease buffer (30 mM NaAc, pH 4.6, 300 mM NaCl, 1 mM ZnSO$_4$, 0.35 mM DTT, 2% glycerol) containing 25 units Mung bean nuclease (Pharmacia). The single-stranded hair-pin DNA is clipped by incubating the reaction at 30° C. for 30 min., followed by addition of 70 ml 10 mM Tris-Cl, pH 7.5, 1 mM EDTA, phenol extraction and precipitation with 2 vols of 96% EtOH and 0.1 vol 3 M NaAc, pH 5.2 on ice for 30 min. Blunt-ending with T4 DNA polymerase: The double-stranded cDNAs are recovered by centrifugation and blunt-ended in 30 ml T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs) by incubating the reaction mixture at 16° C. for 1 hour. The reaction is stopped by addition of EDTA to a final concentration of 20 mM, followed by phenol and chloroform extractions, and precipitation for 12 hours at −20° C. by adding 2 vols 96% EtOH and 0.1 vol 3 M NaAc pH 5.2.

Adaptor ligation, Not I digestion and size selection:

After the fill-in reaction the cDNAs are recovered by centrifugation, washed in 70% EtOH and dried. The cDNA pellet is resuspended in 25 ml ligation buffer (30 mM Tris-Cl, pH 7.8, 10 mM MgCl$_2$, 10 mM DTT, 0.5 mM ATP) containing 2.5 mg non-palindromic BstXI adaptors (Invitrogen) and 30 units T4 ligase (Promega) and incubated at 16° C. for 12 hours. The reaction is stopped by heating at 65° C. for 20 min. and then cooling on ice for 5 min. The adapted cDNA is digested with Not I restriction enzyme by addition of 20 ml water, 5 ml 10× Not I restriction enzyme buffer (New England Biolabs) and 50 units Not I (New England Biolabs), followed by incubation for 2.5 hours at 37° C. The reaction is stopped by heating at 65° C. for 10 min. The cDNAs are size-fractionated by gel electrophoresis on a 0.8% SeaPlaque GTG low melting temperature agarose gel (FMC) in 1 ×TBE to separate unligated adaptors and small cDNAs. The cDNA is size-selected with a cut-off at 0.7 kb and rescued from the gel by use of b-Agarase (New England Biolabs) according to the manufacturer's instructions and precipitated for 12 hours at −20° C. by adding 2 vols 96% EtOH and 0.1 vol 3 M NaAc pH 5.2.

Construction of libraries: The directional, size-selected cDNA is recovered by centrifugation, washed in 70% EtOH, dried and resuspended in 30 ml 10 mM Tris-Cl, pH 7.5, 1 mM EDTA. The cDNAs are desalted by gelfiltration through a MicroSpin S-300 HR (Pharmacia) spin column according to the manufacturer's instructions. Three test ligations are carried out in 10 ml ligation buffer (30 mM Tris-Cl, pH 7.8, 10 MM MgCl$_2$, 10 mM DTT, 0.5 mM ATP) containing 5 ml double-stranded cDNA (reaction tubes #1and #2), 15 units T4 ligase (Promega) and 30 ng (tube #1), 40 ng (tube #2) and 40 ng (tube #3,the vector background control) of BstXI-NotI cleaved pYES 2.0 vector. The ligation reactions are performed by incubation at 16° C. for 12 hours, heating at 70° C. for 20 min. and addition of 10 ml water to each tube. 1 ml of each ligation mixture is electroporated into 40 ml electrocompetent E. coli DH10B cells (Bethesda research Laboratories) as described (Sambrook et al. (1989) Molecular cloning: A laboratory manual, Cold Spring Harbor lab., Cold Spring Harbor, N.Y.). Using the optimal conditions a library is established in E. coli consisting of pools. Each pool is made by spreading transformed E. coli on LB+ampicillin agar plates giving 15.000–30.000 colonies/plate after incubation at 37° C. for 24 hours. 20 ml LB+ampicillin is added to the plate and the cells were suspended herein. The cell suspension is shaked in a 50 ml tube for 1 hour at 37° C. Plasmid DNA is isolated from the cells according to the manufacturer's instructions using QIAGEN plasmid kit and stored at −20° C.

1 ml aliquots of purified plasmid DNA (100 ng/ml) from individual pools are transformed into S. cerevisiae W3124 by electroporation (Becker and Guarante (1991) Methods Enzymol. 194:182–187) and the transformants are plated on SC agar containing 2% glucose and incubated at 30° C.

Identification of positive clones:

The tranformants is plated on SC agar containing 0.1% AZCL galactan (Megazyme, Australia) and 2% Galactose and incubated for 3–5 days at 30° C.

Galactanase positive colonies are identified as colonies surrounded by a blue halo.

Isolation of a cDNA gene for expression in Aspergillus:

A galactanase-producing yeast colony is inoculated into 20 ml YPD broth in a 50 ml glass test tube. The tube is shaken for 2 days at 30° C. The cells are harvested by centrifugation for 10 min. at 3000 rpm.

DNA is isolated according to WO 94/14953 and dissolved in 50 ml water. The DNA is transformed into E. coli by standard procedures. Plasmid DNA is isolated from E. coli using standard procedures, and analyzed by restriction enzyme analysis. The cDNA insert is excised using appropriate restriction enzymes and ligated into an Aspergillus expression vector.

Transformation of Aspergillus oxyzae or Aspergillus niger

Protoplasts may be prepared as described in WO 95/02043, p. 16, line 21–page 17, line 12, which is hereby incorporated by reference.

100 μl of protoplast suspension is mixed with 5–25 μg of the appropriate DNA in 10 μl of STC (1.2 M sorbitol, 10 mM Tris-HCl, pH=7.5, 10 mM CaCl$_2$). Protoplasts are mixed with the aspergillus vector of interest. The mixture is left at room temperature for 25 minutes. 0.2 ml of 60% PEG 4000 (BDH 29576), 10 mM CaCl$_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates (Cove, Biochem. Biophys. Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of A. ozyzae transformants

Each of the transformants are inoculated in 10 ml of YPM (cf. below) and propagated. After 2–5 days of incubation at 30° C., the supernatant is removed. The galactanase activity is identified by applying 10 μl supernatant to 4 mm diameter holes punched out in agar plates containing 0.2% AZCLÔ galactan (MegazymeÔ, Australia). Galactanase activity is then identified as a blue halo. ps Fed batch fermentation:

Fed batch fermentation was performed in a medium comprising maltodextrin as a carbon source, urea as a nitrogen source and yeast extract. The fed batch fermentation was performed by inoculating a shake flask culture of A. oryzae host cells in question into a medium comprising 3.5% of the carbon source and 0.5% of the nitrogen source. After 24 hours of cultivation at pH 7.0 and 34° C. the continuous supply of additional carbon and nitrogen sources were initiated. The carbon source was kept as the limiting factor and it was secured that oxygen was present in excess. The fed batch cultivation was continued for 4 days.

Isolation of the DNA sequence shown in SEQ ID No. 1:

The galactanase encoding part of the DNA sequence shown in SEQ ID No. 1 coding for the galactanase of the invention can be obtained from the deposited organism *Saccharomyces cerevisiae* DSM 9983 by extraction of plasmid DNA by methods known in the art (Sambrook et al. (1989) Molecular cloning: A laboratory manual, Cold Spring Harbor lab., Cold Spring Harbor, N.Y.).

Isolation of the DNA sequence shown in SEQ ID No. 3:

The galactanase encoding part of the DNA sequence shown in SEQ ID No. 3 coding for the galactanase of the invention can be obtained from the deposited organism *Saccharomyces cerevisiae* DSM 9976 by extraction of plasmid DNA by methods known in the art (Sambrook et al. (1989) Molecular cloning: A laboratory manual, Cold Spring Harbor lab., Cold Spring Harbor, N.Y.).

Media

YPD: 10 g yeast extract, 20 g peptone, $H_2O$ to 900 ml. Autoclaved, 100 ml 20% glucose (sterile filtered) added.

YPM: 10 g yeast extract, 20 g peptone, $H_2O$ to 900 ml. Autoclaved, 100 ml 20% maltodextrin (sterile filtered) added.

10×Basal salt: 75 g yeast nitrogen base, 113 g succinic acid, 68 g NaOH, $H_2O$ ad 1000 ml, sterile filtered.

SC-URA: 100 ml 10×Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-agar: SC-URA, 20 g/l agar added.

SC-variant agar: 20 g agar, 20 ml 10×Basal salt, $H_2O$ ad 900 ml, autoclaved

AZCL galactan (Megazyme, Australia)

PEG 4000 (polyethylene glycol, molecular weight=4,000) (BDH, England)

EXAMPLES

Example 1

Cloning and expression of a galactanase from *Myceliophthora thermophila* CBS No. 117.65 mRNA was isolated from *Myceliophthora thermophila*, CBS No. 117.65, grown in cellulose-containing with agitation to ensure sufficient aeration. Mycelia were harvested after 3–5 days' growth, immediately frozen in liquid nitrogen and stored at −80° C. A library from *Myceliophthora thermophila*, CBS No. 117.65, consisting of approx. $9 \times 10^5$ individual clones was constructed in *E. coli* as described with a vector background of 1%. Plasmid DNA from some of the pools was transformed into yeast, and 50–100 plates containing 250–400 yeast colonies were obtained from each pool.

Galactanase-positive colonies were identified and isolated on SC-agar plates with the AZCL xylan assay. cDNA inserts were amplified directly from the yeast colonies and characterized as described in the Materials and Methods section above. The DNA sequence of the cDNA encoding the galactanase is shown in SEQ ID No. 1 and the corresponding amino acid sequence is shown in SEQ ID No. 2. In SEQ ID No. 1 DNA nucleotides from No 1-1050 define the galactanase encoding region.

The cDNA is obtainable from the plasmid in DSM 9983.

Total DNA was isolated from a yeast colony and plasmid DNA was rescued by transformation of *E. coli* as described above. In order to express the galactanase in Aspergillus, the DNA was digested with appropriate restriction enzymes, size fractionated on gel, and a fragment corresponding to the galactanase gene was purified. The gene was subsequently ligated to pHD414, digested with appropriate restriction enzymes, resulting in the plasmid pA2G53.

After amplification of the DNA in *E. coli* the plasmid was transformed into *Aspergillus oryzae* as described above.

Test of *A. oxyzae* transformants

Each of the transformants were tested for enzyme activity as described above. Some of the transformants had galactanase activity which was significantly larger than the *Aspergillus oryzae* background. This demonstrates efficient expression of the galactanase in *Aspergillus oryzae*.

Example 2

A homology search with a DNA sequence (shown in SEQ ID No 1) encoding a galactanase of the invention against nucleotide and protein databases was performed. The homology search showed that the most related galactanase was a β-1,4-galactanase from *Aspergillus aculeatus*.

According to the method described in the "DETAILED DESCRIPTION OF THE INVENTION" the DNA homology of a galactanase of the invention ( against most prior art galactanases) was determined using the computer program GAP. The galactanase of the invention has only 59% DNA homology to the beta-1,4-galactanase from *Aspergillus aculeatus* (WO 92/13945). This show that the galactanase of the invention indeed is distant from any known galactanases.

Example 3

Purification of recombinant galactanases from *M. themaphilum*.

The culture supernatant from the fermentation of *Aspergillus oryzae* expressing the recombinant enzyme was centrifuged and filtered through a 0.2 μm filter to remove the mycelia. 250 ml of the filtered supernatant was ultrafiltered in a Filtron ultracette or Amicon ultrafiltration device with a 10kDa membrane and at the same time the buffer was changed to 25 mM Tris-HCl pH 8.0 in two successive rounds of ultrafiltration in the same device. The resulting 40 ml sample was loaded at 1.5 ml/min onto a Pharmacia HR16/20 Fast Flow Q Sepharose anion exchange column equilibrated in 25 mM Tris-HCl pH 8.0. After the sample was applied, the column was washed with two column volumes 25 mM Tris-HCl pH 8.0 and bound proteins were eluted with a linear increasing NaCl gradient from 0 to 0.5 M NaCl in 25 mM Tris-HCl pH 8.0. Fractions were tested for galactanase activity on AZCL-galactan and fractions containing the activity were pooled.

The *M. thermophilum* galactanase was not retained on the column and the wash fraction from the anion exchange step was collected and concentrated and buffer exchanged into 10 mM Sodium Citrate pH 4.0. This material was loaded at 1.5 ml/min onto a Pharmacia HR16/20 Fast Flow S Sepharose cation exchange column equilibrated in 10 mM Sodium citrate pH 4.0. After the sample was applied, the column was washed with two column volumes of the same buffer and bound proteins were eluted with a linear NaCl gradient from 0 to 0.35 M NaCl in 10 mM Sodium citrate pH 4.0. The galactanase activity eluted at approximately 0.1 M NaCl and the fractions containing the activity were concentrated on a Filtron Macrosep 10 kDa ultrafiltration device to 500 μl. 450 μl was loaded at 0.5 ml/min onto a Pharmacia HR10/30 Superdex 75 gelfiltration column and the proteins were eluted at 0.5 ml/min with 0.25 M amoniumacetate, pH 5.5. The *M. thermophilum* galactanase was eluted in electrophoretically pure form from the column.

Protein concentration is determined by use of the "Bio-Rad protein assay" in accordance with the Manufactures (Bio-Rad Laboratories GmbH) recommendations.

Example 4
Characterization of Recombinant Galactanases from *M. thermophilum*

The Molecular weight and iso-electric point of the enzymes was determined as described in WO 94/21785.

The activities of the enzymes were measured either by the release of reducing sugars from lupin galactan (MegaZyme, Australia) or by the release of blue colour from AZCL-potato-galactan (MegaZyme, Australia).

0.5 ml 0.4% AZCL-potato-galactan was mixed with 0.5 ml 0.1 M citrate/phosphate buffer of optimal pH and 10 μl of a suitably diluted enzyme solution was added. Incubations were carried out in Eppendorf Thermomixers for 15 minutes at 30° C. (if not otherwise specified) before heat-inactivation of the enzymes at 95° C. for 20 minutes. Enzyme incubations were carried out in triplicate and a blank was produced in which enzyme was added but immediately inactivated. After centrifugation the absorbance of the supernatant was measured in microtiter plates at 620 nm and the blank value was subtracted.

0.5% solutions of lupin galactan were made in 0.1 M citrate/phosphate of the optimal pH (if not otherwise specified), 10 μl of suitably diluted enzyme solution was added to 1 ml of substrate and incubations were carried out at 30° C. for 15 minutes before heat-inactivation at 95° C. for 20 minutes. Reducing sugars were determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Results of blanks were subtracted. Galactose was used as a standard.

pH and temperature optimums were measured on AZCL-galactan. 0.1 M citrate/phosphate buffers of pH (2.5, 3.0, 3.5, 4.0, 4.5, 5.0, 5.5, 6.0, 6.5, 7.0, 7.5, 8.0, 8.5, 9.0, 9.5, 10.0) were used for determination of pH optimum. In order to determine the temperature optimum, 0.1 M citrate/phosphate buffers at optimal pH were used for reaction at different temperatures for 15 minutes.

Km and specific activity was found by carrying out incubations at lupin galactan concentrations (S) ranging from 0.025 to 1.5% and measure the reducing sugars produced, then calculate the reaction rate (v), picture S/v as a function of S, carry out linear regression analysis, finding the slope (=1/Vmax) and the intercept (Km/Vmax) and calculating Km and the specific activity (=Vmax/E), where E is the amount of enzyme added.

| Enzyme | *M. thermophilum* |
| --- | --- |
| Mw | 42 kDa |
| pI | 7.8 |
| pH optimum | 6.0 |
| temperature optimum | 70° C. |
| Km (% galactan) | 0.5–0.9 |
| Specific activity (μmol/min/mg) | 800–1200 |

Aminoterminal sequence

Aminoterminal analysis was determined by using Edman degradation with Applied Biosystem equipment (ABI 473A protein sequencer, Applied Biosytem, U.S.A.) carried out as described by manufacturer.

N-terminal sequence(s):

For the galactanase of the invention having the amino acid sequence shown in SEQ ID NO 2 the N-terminal sequence is:

N-terminal Ala-Leu-Thr-Tyr-Arg-Gly-Val-

The N-terminal amino acid Ala is position 19 in SEQ ID NO 2. This indicates the mature galactanase enzyme of the invention starts at position 19 in SEQ ID No 2.

Consequently the mature sequence is from 19–350 in SEQ ID no 2.

Example 5
Cloning and Expression of a Galactanase from *Humicola insolens* 1800 mRNA was isolated from *Humicola insolens*, DSM 1800, grown in a maize grits-containing fermentation medium with agitation to ensure sufficient aeration. Mycelia were harvested after 3–5 days' growth, immediately frozen in liquid nitrogen and stored at −80° C. A library from *Humicola insolens*, DSM No. 1800, consisting of approx. 9×10$^5$ individual clones was constructed in *E. coli* as described with a vector background of 1%. Plasmid DNA from some of the pools was transformed into yeast, and 50–100 plates containing 250–400 yeast colonies were obtained from each pool.

Galactanase-positive colonies were identified and isolated on SC-agar plates with the AZCL xylan assay. cDNA inserts were amplified directly from the yeast colonies and characterized as described in the Materials and Methods section above. The DNA sequence of the cDNA encoding the galactanase is shown in SEQ ID No. 3 and the corresponding amino acid sequence is shown in SEQ ID No. 4.

The cDNA is obtainable from the plasmid in DSM 9976.

Total DNA was isolated from a yeast colony and plasmid DNA was rescued by transformation of *E. coli* as described above. In order to express the galactanase in Aspergillus, the DNA was digested with appropriate restriction enzymes, size fractionated on gel, and a fragment corresponding to the galactanase gene was purified. The gene was subsequently ligated to pHD414, digested with appropriate restriction enzymes, resulting in the plasmid pA2G51.

After amplification of the DNA in *E. coli* the plasmid was transformed into *Aspergillus oryzae* as described above.

Test Of *A. oryzae* Transfozmants

Each of the transformants were tested for enzyme activity as described above. Some of the transformants had galactanase activity which was significantly larger than the *Aspergillus oryzae* background. This demonstrates efficient expression of the galactanase in *Aspergillus oryzae*.

Example 6

A homology search with a DNA sequence (shown in SEQ ID No 3) encoding a galactanase of the invention against nucleotide and protein databases was performed. The homology search showed that the most related galactanase was a b-1,4-galactanase from *Aspergillus aculeatus*.

According to the method described in the "DETAILED DESCRIPTION OF THE INVENTION" the DNA homology of the galactanase of the invention against most prior art galactanases was determined using the computer program GAP. The galactanase of the invention has only 55% DNA homology to the b-1,4-galactanase from *Aspergillus aculeatus* (WO 92/13945). This show that the galactanase of the invention indeed is distant from any known galactanases.

Example 7
Purification of Recombinant Galactanases from *H. insolens*

The culture supernatants from the fermentation of *Aspergillus oryzae* expressing the recombinant enzymes were centrifuged and filtered through a 0.2 μm filter to remove the mycelia. 250 ml of the filtered supernatant was ultrafiltered in a Filtron ultracette or Amicon ultrafiltration device with a 10 kDa membrane and at the same time the buffer was changed to 25 mM Tris-HCl pH 8.0 in two successive rounds of ultrafiltration in the same device. The resulting 40 ml sample was loaded at 1.5 ml/min onto a Pharmacia HR16/20 Fast Flow Q Sepharose anion exchange column equilibrated in 25 mM Tris-HCl pH 8.0. After the sample was applied, the column was washed with two column volumes 25 mM Tris-HCl pH 8.0 and bound proteins were eluted with a linear increasing NaCl gradient from 0 to 0.5 M NaCl in 25 mM Tris-HCl pH 8.0. Fractions were tested for galactanase activity on AZCL-galactan and fractions containing the activity were pooled.

The *H.insolens* galactanase was retained on the column and was eluted with NaCl in electrophoretically pure form.

Protein concentration is determined by use of the "Bio-Rad protein assay" in accordance with the Manufactures (Bio-Rad Laboratories GmbH) recommendations.

Example 8

Characterization of Recombinant Galactanases from *H. insolens*

The Molecular weight and iso-electric point of the enzymes was determined as described in WO 94/21785.

The activities of the enzymes were measured either by the release of reducing sugars from lupin galactan (MegaZyme, Australia) or by the release of blue colour from AZCL-potato-galactan (MegaZyme, Australia).

0.5 ml 0.4% AZCL-potato-galactan was mixed with 0.5 ml 0.1 M citrate/phosphate buffer of optimal pH and 10 µl of a suitably diluted enzyme solution was added. Incubations were carried out in Eppendorf Thermomixers for 15 minutes at 30° C. (if not otherwise specified) before heat-inactivation of the enzymes at 95° C. for 20 minutes. Enzyme incubations were carried out in triplicate and a blank was produced in which enzyme was added but immediately inactivated. After centrifugation the absorbance of the supernatant was measured in microtiter plates at 620 nm and the blank value was subtracted.

0.5% solutions of lupin galactan were made in 0.1 M citrate/phosphate of the optimal pH (if not otherwise specified), 10 µl of suitably diluted enzyme solution was added to 1 ml of substrate and incubations were carried out at 30° C. for 15 minutes before heat-inactivation at 95° C. for 20 minutes. Reducing sugars were determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Results of blanks were subtracted. Galactose was used as a standard.

pH and temperature optimums were measured on AZCL-galactan. 0.1 M citrate/phosphate buffers of pH (2.5, 3.0, 3.5, 4.0, 4.5, 5.0, 5.5, 6.0, 6.5, 7.0, 7.5, 8.0, 8.5, 9.0, 9.5, 10.0) were used for determination of pH optimum. In order to determine the temperature optimum, 0.1 M citrate/phosphate buffers at optimal pH were used for reaction at different temperatures for 15 minutes.

Km and specific activity were found by carrying out incubations at lupin galactan concentrations (S) ranging from 0.025 to 1.5% and measure the reducing sugars produced, then calculate the reaction rate (v), picture S/v as a function of S, carry out linear regression analysis, finding the slope (=1/Vmax) and the intercept (Km/Vmax) and calculating Km and the specific activity (=Vmax/E), where E is the amount of enzyme added.

| Enzyme | *H. insolens* |
|---|---|
| Mw | 44 kDa |
| pI | 8.5 |
| pH optimum | 7.5 |
| temperature optimum | 60° C. |
| Km (% galactan) | 0.7–1.0 |
| Specific activity (µmol/min/mg) | 475–575 |

Aminoterminal Sequence

Aminoterminal analysis was determined by using Edman degradation with Applied Biosystem equipment (ABI 473A protein sequencer, Applied Biosytem, U.S.A.) carried out as described by manufacturer.

N-terminal sequencers):

For the galactanase of the invention having the amino acid sequence shown in SEQ ID NO 4 the N-terminal sequence is:

N-terminal Leu-Gln-Tyr-Lys-Gly-Val-Asp-

The N-terminal amino acid Gln is position 19 in SEQ ID NO 4. This indicates the mature galactanse enzyme of the invention starts at position 19 in SEQ ID No 4.

Consequently the mature sequence is from 19–349 in SEQ ID no 4.

Example 9

The effect of galactanase on animal feed

The galactanase used in this experiment was the galactanas of the invention obtained from *H. insolens,* and purified as described in example 7.

The Lactase used in the experiment was a commercial Lactase named Sumilact L (Shinnihon Japan).

Wistar male rats (66–68 g) are divided in to groups of 5, with the average weight of the treatments not exceeding ±0.5 g. Rats are housed in individual metabolism cages with separate collection of urine and faeces. The experimental period is divided in to a 4 day acclimatization period, allowing the rats to adapt to the cages and the feed and a 4 day balance period, where faeces and urine is collected daily.

Ten g DM (Dry matter) are fed per animal per day. The diet consisted of 600 g/kg of lupins and 400 g/kg of a N-free mix (8.9% cane sugar, 5.2% cellulose powder, 5.2% vegetable oil, 80.7% corn starch), vitamins, minerals and 1.2 g DL-methionine. Methionine is added to stimulate the appetite, since lupins are very low in sulfur-containing amino acids. Rats are fed once daily at the same time.

At the end of the experimental period the animals are weighed individually and killed with $CO_2$.

Dry matter content of the diet and faeces was determined by lyophilisation.

Nitrogen content of the diet, urine and faeces samples was determined by Kjeltec methods of digestion, distillation and titration.

The results of the trial, determined as the true digestibility of the protein and the DM digestibility is presented in table 1. Below:

| Diet | Apparent protein digestibility | DM digestibility |
| --- | --- | --- |
| Control | 80.99 | 75.94 |
| 10.6 g Galactanase | 83.84 | 77.08 |
| 32.0 g Galactanase | 84.19 | 75.90 |
| 10.6 g Galactanase + 1 g Lactase | 84.65 | 76.16 |
| 32.0 g Galactanase + 1 g Lactase | 84.39 | 73.90 |

The dose is in g galactanase or lactase preparation/kg of lupin in the diet.

Example 10
Isolation of PCR Fragment Specific for a Galactanase Gene of a Strain of the Order Sordariales Two amino acid motifs in the amino acid sequences of the two galactanases (having the amino acid sequences shown in SEQ ID No 2 and 4) obtained from Sordariales was identified;

a) Ser(S)-Asp(D)-Thr(T)-Trp(W)-Ala(A)-Asp(D)-Pro(P)-Ala(A)-His(H) (Pos. 101–109 in SEQ ID 2, and Pos. 100–108 in SEQ ID 4);

b) Phe(F)-Tyr(Y)-Trp(W)-Glu(E)-Pro(P)-Ala(A)-Trp(W)-Ile(I) (Pos. 312–319 in SEQ ID 2, and Pos. 311–318 in SEQ ID 4);

A computer analysis in the SWISS-PROT amino acid database was performed in order to investigate if the two above mentioned motifs already existed in the prior art.

None of the two motifs were identified, which of course too showed that these motifs are not in the prior art fungal galactanase amino acid sequence from *Aspergillus acuelatus* (WO 92/13945).

Degenerated PCR DNA primers was made based on the above mentioned two motifs, a) "5'-CTA TTC GGA TCC AG(C/T) GA(C/T) AC(A/C) TGG GC(G/C) GA(C/T) CC(G/T) GC(G/T) C-3'" [SEQID NO 5] the sense primer; and b) "5'-CTA ATG TCT AGA (A/G)AT CCA (A/G/C/T)GC (A/G/C/T)GG (C/T)TC CCA (A/G)TA AAA-3'" [SEQID NO 6] the anti-sense primer.

(Sequence in bold are linker seq. to facilitate cloning of the PCR fragment).

3 separate PCR amplifications was performed with above primers and with cDNA libraries from *Aspergillus acuelatus* CBS 101.43, *Myceliophthora thermophila* CBS No. 117.65, and *Humicola insolens* DSM No. 1800. Around 10 ng of DNA was used as template DNA in each of the 3 PCR reaction.

The cDNA library from *Myceliophthora thermophila* CBS No. 117.65, and *Humicola insolens* DSM No. 1800 was made as described herein. The cDNA library from *Aspergillus acuelatus* CBS 101.43 was made as described in WO 92/13945.

The Tag-Start kit from Clontech was used according to the manufactures protocol. Primer concentrations were 0.5 mM for both primers above. Touch-down PCR was used for amplification (Don, R. H. et al. (1991), Nucleic Acids Res. 19:4008). First the DNA was denatured for 3 min. at 95° C. then two cycles were done at each of the following annealing temperatures: 60° C., 59° C., 58° C., 57° C., 56° C., 55° C., 54° C., 53° C., 52° C. and 51° C., with an annealing time of one min. each. Prior to annealing the incubation was heated to 95° C. for one min and after annealing elongation was performed for 30 sec at 72° C. Cycles 21 to 35 were performed as follows: denaturation one min. at 95° C., annealing one min at 50° C. and elongation for 30 sec at 72° C.

From each of the two separate PCR reactions performed with *Myceliophthora thermophila* CBS No. 117.65, and *Humicola insolens* DSM No. 1800 DNA as template DNA, a PCR band of approximately 700 bp was obtained, where in the PCR reaction with *Aspergillus acuelatus* CBS 101.43 DNA as template no specific PCR band was obtained.

This illustrate that the above two identified motifs and corresponding deduced degenerated primers are specific for galactanases from Sordariales.

It is presently believed that it is possible to clone other galactanase from a strain of the genus Sordariales by e.g. use any of the two generated PCR fragments above as probe in a standard hybridization cloning method.

What is claimed is:

1. A DNA construct comprising a DNA sequence encoding a galactanase, wherein said galactanase is derived from *Myceliopthora thermophila* or *Humicola insolens* and has a pH optimum above 5.9.

2. A DNA construct encoding an enzyme exhibiting galactanase activity, wherein said DNA sequence hybridizes with a probe under conditions of hybridization in 5×SSC at 45° C. and washing in 2×SSC at 55° C., wherein said probe is a product of a PCR reaction using as a template DNA isolated from *Humicola insolens* (DSM 1800) or DNA isolated from *Myceliophthora thermophila* (CBS 117.65) and using as PCR primers:

5'-CTA TTC GGA TCC AG(C/T) GA(C/T) AC(A/C) TGG GC(G/C) GA(C/T) CC(G/T) GC(G/T) C-3' SEQ ID NO:5 as the sense primer, and 5'-CTA ATG TCT AGA (A/G)AT CCA (A/G/C/T)GC (A/G/C/T)GG (C/T)TC CCA (A/G)TA AAA-3' SEQ ID NO:6 as the anti-sense primer.

3. The DNA construct according to claim 2, wherein the enzyme encoded by said DNA sequence comprises an amino acid sequence selected from the group consisting of a) Ser(S)-Asp(D)-Thr(T)-Trp(W)-Ala(A)-Asp(D)-Pro(P)-Ala(A)-His(H);

b) Phe(F)-Tyr(Y-Tip(W)-Glu(E)-Pro(P)-Ala(A)-Trp(W)-Ile(I); and both a) and b).

4. A DNA construct comprising a DNA sequence encoding an enzyme exhibiting galactanase activity, wherein said DNA sequence is selected from the group consisting of:

(a) the galactanase encoding part of the DNA sequence cloned into plasmid pYES 2.0 present in *Saccharomyces cerevisiae* DSM 9983;

(b) the DNA sequence shown in positions 1–1050 in SEQ ID NO 1 or its complementary strand;

(c) an analogue of the DNA sequence defined in (a) or (b) which is at least 80% homologous with said DNA sequence, wherein said homology is determined using GAP with a GAP creation penalty of 5.0 and a GAP extension penalty of 0.3;

(d) a DNA sequence which hybridizes with the DNA sequence shown in positions 1–1050 in SEl ID NO 1 under conditions of hybridization in 5×SSC at 45° C. and washing in 2×SSC, 0.5% SDS at 65° C.;

(e) a DNA sequence which codes for a polypeptide having the same amino acid sequence as the polypeptide encoded by any of DNA sequences (a)–(d); and (f) a DNA sequence which is a fragment of the DNA sequences specified in (a), (b), (c), (d), or (e);

wherein said DNA sequence encodes a polypeptide exhibiting galactanase activity.

5. A DNA construct comprising a DNA sequence encoding an enzyme exhibiting galactanase activity, wherein DNA sequence is selected from the group consisting of:

(a) the galactanase encoding part of the DNA sequence cloned into plasmid pYES 2.0 present in *Saccharomyces cerevisiae* DSM 9976;

(b) the DNA sequence shown in positions 1–1047 in SEQ ID NO 3 or its complementary strand;

(c) an analogue of the DNA sequence defined in (a) or (b) which is at least 80% homologous with said DNA sequence, wherein said homology is determined using GAP with a GAP creation penalty of 5.0 and a GAP extension penalty of 0.3;

(d) a DNA sequence which hybridizes with the DNA sequence shown in positions 1–1047 in SEQ ID NO 3 under conditions of hybridization in 5×SSC at 45° C. and washing in 2×SSC, 0.5% SDS at 65° C.;

(e) a DNA sequence which codes for a polypeptide having the same amino acid sequence as the polypeptide encoded by any of DNA sequences (a)–(d); and (f) a DNA sequence which is a fragment of the DNA sequences specified in (a), (b), (c), (d), or (e), wherein said DNA sequence encodes a polypeptide exhibiting galactanase activity.

6. A recombinant expression vector comprising a DNA construct according to claim 1.

7. A host cell comprising a recombinant expression vector according to claim 6.

8. The host cell according to claim 6, wherein said cell is a fungal cell.

9. The cell according to claim 8, wherein said cell is selected from the group consisting of Fusarium, Aspergillus, and Trichodenna.

10. A method of producing an enzyme exhibiting galactanase activity, the method comprising culturing a cell according to claim 7 under conditions permitting the production of the enzyme, and recovering the enzyme from the culture.

11. A DNA construct comprising a DNA sequence shown in positions 55–1050 of SEQ ID NO:1.

12. A recombinant expression vector comprising a DNA construct according to claim 2.

13. A host cell comprising a recombinant expression vector according to claim 12.

14. A method of producing an enzyme exhibiting galactanase activity, the method comprising culturing a cell according to claim 13 under conditions permitting the production of the enzyme, and recovering the enzyme from the culture.

15. A recombinant expression vector comprising a DNA construct according to claim 4.

16. A host cell comprising a recombinant expression vector according to claim 15.

17. A method of producing an enzyme exhibiting galactanase activity, the method comprising culturing a cell according to claim 16 under conditions permitting the production of the enzyme, and recovering the enzyme from the culture.

18. A recombinant expression vector comprising a DNA construct according to claim 5.

19. A host cell comprising a recombinant expression vector according to claim 18.

20. A method of producing an enzyme exhibiting galactanase activity, the method comprising culturing a cell according to claim 19 under conditions permitting the production of the enzyme, and recovering the enzyme from the culture.

21. The DNA construct according to claim 1, wherein said galactanase has a pH optimum between 6.0–10.

22. The DNA construct according to claim 21, wherein said galatanase has a pH optimum between 7.5–10.

23. The DNA construct according to claim 2, wherein said conditions of hybridization comprise washing in 2×SSC, 0.5% SDS at 70°C.

24. The DNA construct according to claim 2, wherein said conditions of hybridization comprise washing in 2×SSC, 0.5% SDS at 75°C.

25. The DNA construct according to claim 4, wherein said conditions of hybridization comprise washing in 2×SSC, 0.5% SDS at 70°C.

26. The DNA construct according to claim 4, wherein said conditions of hybridization comprise washing in 2XSSC, 0.5% SDS at 75°C.

27. The DNA construct according to claim 4, wherein the analogue of (c) is at least about 90% homologous with said DNA sequences.

28. The DNA construct according to claim 27, wherein the analogue of (c) is at least about 95% homologous with said DNA sequences.

29. The DNA construct according to claim 28, wherein the analogue of (c) is at least about 97% homologous with said DNA sequences.

30. The DNA construct according to claim 5, wherein said conditions of hybridization comprise washing in 2XSSC, 0.5% SDS at 70°C.

31. The DNA construct according to claim 5, wherein said conditions of hybridization comprise washing in 2XSSC, 0.5SDS at 75°C.

32. The DNA construct according to claim 5, wherein the analogue of (c) is at least about 90% homologous with said DNA sequences.

33. The DNA construct according to claim 32, wherein the analogue of (c) is at least about 95% homologous with said DNA sequences.

34. The DNA construct according to claim 33, wherein the analogue of (c) is at least about 97% homologous with said DNA sequences.

* * * * *

SEQUENCE LISTING

<160> NUMBER OF SEQ ID NOS: 6

<210> SEQ ID NO 1
<211> LENGTH: 1050
<212> TYPE: DNA
<213> ORGANISM: Myceliophthora thermophila

<400> SEQUENCE: 1

```
atgatgctca cacgcttcgt ggctggcctg ctcggcatct ccgccgcgga tgccgccctc      60
acctacagag gcgtggattg gtcctcagtg gtggttgagg aacgggccgg cgtctcgtac     120
aagaacacca acgggaatgc ccaaccgctt gagaacatcc tggctgccaa tggcgtcaac     180
acggtgcggc agcgagtctg ggttaacccc gcggacggca actacaacct cgactacaac     240
atcgcgatcg cgaagagggc gaaggctgcc gggcttggcg tgtacatcga cttccactac     300
agcgacacct gggccgatcc tgctcatcag accatgcccg ctgggtggcc gagcgacatt     360
gacaacctct cctggaagct ctacaactac actctggacg ccgccaacaa gctccagaac     420
```

```
gcgggtatcc agcccaccat cgtgtccatc ggtaacgaga tccggccgg tctgctatgg    480 cccacaggga gaaccgagaa ctgggccaac attgcccggt tgttgcactc cgctgcttgg    540
ggtatcaagg actcgtcgct cagcccgaag ccaaagatca tgatccacct cgacaacgga    600
tgggactggg gtaccagaa ttggtggtac acgaatgtct tgaagcaggg tacacttgag    660
ctgtccgact gtgacatgat gggcgtctcg ttctacccct tttactcgtc gtcggcaacc    720
ttgagcgccc tgaaatcgag cttggacaac atggccaaaa cctggaacaa ggagattgcc    780
gtggtcgaga ccaattggcc aatctcttgt cccaacccaa ggtacagttt ccctcggac    840 gtcaagaaca tccccttctc gccggaagga cagacgacct tcatcaccaa cgtggccaac    900
atcgtgtcct cggtaagccg cggcgtaggc ctgttttatt gggaacccgc ttggattcac    960
aatgcaaacc tgggctcgtc gtgcgccgac aacaccatgt tttcgcaatc cgggcaggct   1020
ttgtccagct tgtccgtttt ccagagaatc                                    1050
```

<210> SEQ ID NO 2
<211> LENGTH: 350
<212> TYPE: PRT
<213> ORGANISM: Myceliophthora thermophila

<400> SEQUENCE: 2

```
Met Met Leu Thr Arg Phe Val Ala Gly Leu Leu Gly Ile Ser Ala Ala
1               5                   10                  15

Asp Ala Leu Thr Tyr Arg Gly Val Asp Trp Ser Ser Val Val
            20                  25                  30

Glu Glu Arg Ala Gly Val Ser Tyr Lys Asn Thr Asn Gly Asn Ala Gln
        35                  40                  45

Pro Leu Glu Asn Ile Leu Ala Ala Asn Gly Val Asn Thr Val Arg Gln
    50                  55                  60

Arg Val Trp Val Asn Pro Ala Asp Gly Asn Tyr Asn Leu Asp Tyr Asn
65                  70                  75                  80

Ile Ala Ile Ala Lys Arg Ala Lys Ala Ala Gly Leu Gly Val Tyr Ile
                85                  90                  95

Asp Phe His Tyr Ser Asp Thr Trp Ala Asp Pro Ala His Gln Thr Met
            100                 105                 110

Pro Ala Gly Trp Pro Ser Asp Ile Asp Asn Leu Ser Trp Lys Leu Tyr
        115                 120                 125

Asn Tyr Thr Leu Asp Ala Ala Asn Lys Leu Gln Asn Ala Gly Ile Gln
    130                 135                 140

Pro Thr Ile Val Ser Ile Gly Asn Glu Ile Arg Ala Gly Leu Leu Trp
145                 150                 155                 160

Pro Thr Gly Arg Thr Glu Asn Trp Ala Asn Ile Ala Arg Leu Leu His
                165                 170                 175

Ser Ala Ala Trp Gly Ile Lys Asp Ser Ser Leu Ser Pro Lys Pro Lys
            180                 185                 190

Ile Met Ile His Leu Asp Asn Gly Trp Asp Trp Gly Thr Gln Asn Trp
        195                 200                 205

Trp Tyr Thr Asn Val Leu Lys Gln Gly Thr Leu Glu Leu Ser Asp Cys
    210                 215                 220

Asp Met Met Gly Val Ser Phe Tyr Pro Phe Tyr Ser Ser Ser Ala Thr
225                 230                 235                 240

Leu Ser Ala Leu Lys Ser Ser Leu Asp Asn Met Ala Lys Thr Trp Asn
                245                 250                 255
```

```
Lys Glu Ile Ala Val Val Glu Thr Asn Trp Pro Ile Ser Cys Pro Asn
            260                 265                 270
Pro Arg Tyr Ser Phe Pro Ser Asp Val Lys Asn Ile Pro Phe Ser Pro
        275                 280                 285
Glu Gly Gln Thr Thr Phe Ile Thr Asn Val Ala Asn Ile Val Ser Ser
    290                 295                 300
Val Ser Arg Gly Val Gly Leu Phe Tyr Trp Glu Pro Ala Trp Ile His
305                 310                 315                 320
Asn Ala Asn Leu Gly Ser Ser Cys Ala Asp Asn Thr Met Phe Ser Gln
                325                 330                 335
Ser Gly Gln Ala Leu Ser Ser Leu Ser Val Phe Gln Arg Ile
            340                 345                 350
```

<210> SEQ ID NO 3
<211> LENGTH: 1047
<212> TYPE: DNA
<213> ORGANISM: Humicola insolens

<400> SEQUENCE: 3

```
atgcgcgcgc ttctgtctac tctcctcctc ggcctcgcga cggccgtcga cgccctccaa      60
tacaagggcg ttgactggtc gtccgtcatg gtcgaggagc gggcgggtgt ccgctacaag     120
aacgtcaacg gccaggagaa gccgctcgag tacatcctgg ccgagaacgg cgtcaacatg     180
gtgcggcagc gcgtctgggt caacccgtgg gacggcaact acaacctcga ctacaacatc     240
cagctcgcgc ggcggaccaa ggcggccggt ctgggcctct acatcaactt ccactacagc     300
gacacctggg ccgacccggc gcaccagacc acgccggccg gtggccgtc cgacatcaac      360
aacctgtcct ggaagctgta caactacacc ctcgactcga tgaaccggtt cgccgacgct     420
gggatccagg tcgacatcgt ctccatcggc aacgagatca cccagggcct gctgtggccc     480
ctgggcaaga ccaacaactg gtacaacatc gcgaggctgc tgcactcggc cgcgtggggc     540
gtcaaggact cgaggctgaa ccccaagccc aagatcatgg tgcacctgga caacggatgg     600
aactgggaca ccccaaactg gtggtacacc aacgtgctgt cccaaggccc cttcgagatg     660
tccgacttcg acatgatggg cgtgtccttc tacccctct actcggcctc ggcgacgctg      720
gactcgctgc gccggagcct caacaacatg gtgtcacgct ggggcaagga ggtggccgtg     780
gtcgagacca actggcccac gtcgtgcccg tatccgcgct accagttccc ggccgacgtc     840
cgcaacgtgc ccttctcagc ggccgggcag acgcagtaca tccagagcgt tgcgaacgtg     900
gtgtcgtcgg tcagcaaggg agtggggctg ttttactggg agccggcgtg gattcacaat     960
gccaacctgg ggtcgtcgtg cgcggataac accatgttta cgccgtcggg tcaggcattg    1020
tcgagtttgt cggtgttcca taggatt                                         1047
```

<210> SEQ ID NO 4
<211> LENGTH: 349
<212> TYPE: PRT
<213> ORGANISM: Humicola insolens

<400> SEQUENCE: 4

```
Met Arg Ala Leu Leu Ser Thr Leu Leu Leu Gly Leu Ala Thr Ala Val
1               5                   10                  15
Asp Ala Leu Gln Tyr Lys Gly Val Asp Trp Ser Ser Val Met Val Glu
            20                  25                  30
Glu Arg Ala Gly Val Arg Tyr Lys Asn Val Asn Gly Gln Glu Lys Pro
        35                  40                  45
```

```
Leu Glu Tyr Ile Leu Ala Glu Asn Gly Val Asn Met Val Arg Gln Arg
     50                  55                  60

Val Trp Val Asn Pro Trp Asp Gly Asn Tyr Asn Leu Asp Tyr Asn Ile
 65                  70                  75                  80

Gln Leu Ala Arg Arg Ala Lys Ala Ala Gly Leu Gly Leu Tyr Ile Asn
                 85                  90                  95

Phe His Tyr Ser Asp Thr Trp Ala Asp Pro Ala His Gln Thr Thr Pro
                100                 105                 110

Ala Gly Trp Pro Ser Asp Ile Asn Asn Leu Ala Trp Lys Leu Tyr Asn
            115                 120                 125

Tyr Thr Leu Asp Ser Met Asn Arg Phe Ala Asp Ala Gly Ile Gln Val
        130                 135                 140

Asp Ile Val Ser Ile Gly Asn Glu Ile Thr Gln Gly Leu Leu Trp Pro
145                 150                 155                 160

Leu Gly Lys Thr Asn Asn Trp Tyr Asn Ile Ala Arg Leu Leu His Ser
                165                 170                 175

Ala Ala Trp Gly Val Lys Asp Ser Arg Leu Asn Pro Lys Pro Lys Ile
            180                 185                 190

Met Val His Leu Asp Asn Gly Trp Asn Trp Asp Thr Gln Asn Trp Trp
        195                 200                 205

Tyr Thr Asn Val Leu Ser Gln Gly Pro Phe Glu Met Ser Asp Phe Asp
    210                 215                 220

Met Met Gly Val Ser Phe Tyr Pro Phe Tyr Ser Ala Ser Ala Thr Leu
225                 230                 235                 240

Asp Ser Leu Arg Arg Ser Leu Asn Asn Met Val Ser Arg Trp Gly Lys
                245                 250                 255

Glu Val Ala Val Val Glu Thr Asn Trp Pro Thr Ser Cys Pro Tyr Pro
            260                 265                 270

Arg Tyr Gln Phe Pro Ala Asp Val Arg Asn Val Pro Phe Ser Ala Ala
        275                 280                 285

Gly Gln Thr Gln Tyr Ile Gln Ser Val Ala Asn Val Val Ser Ser Val
    290                 295                 300

Ser Lys Gly Val Gly Leu Phe Tyr Trp Glu Pro Ala Trp Ile His Asn
305                 310                 315                 320

Ala Asn Leu Gly Ser Ser Cys Ala Asp Asn Thr Met Phe Thr Pro Ser
                325                 330                 335

Gly Gln Ala Leu Ser Ser Leu Ser Val Phe His Arg Ile
            340                 345

<210> SEQ ID NO 5
<211> LENGTH: 37
<212> TYPE: DNA
<213> ORGANISM: Artificial Sequence
<220> FEATURE:
<221> NAME/KEY: mutation
<222> LOCATION: (0)...(0)
<223> OTHER INFORMATION: y is t/u or c
      m is a or c
      s is g or c
      k is g or t/u

<400> SEQUENCE: 5
ctattcggat ccagygayac mtgggcsgay cckgckc                    37

<210> SEQ ID NO 6
<211> LENGTH: 36
<212> TYPE: DNA
<213> ORGANISM: Artificial Sequence
```

```
-continued

<220> FEATURE:
<221> NAME/KEY: mutation
<222> LOCATION: (0)...(0)
<223> OTHER INFORMATION: r is g or a
      n is a or g or c or t/u
      y is t/u or c

<400> SEQUENCE: 6
ctaatgtcta garatccang cnggytccca rtaaaa                              36
```